US012653503B2

(12) United States Patent
Savord et al.

(10) Patent No.:  US 12,653,503 B2
(45) Date of Patent:  Jun. 16, 2026

(54) ULTRASOUND IMAGING SYSTEM INCLUDING CONFIGURABLE TRANSDUCER PROBE

(71) Applicant: KONINKLIJKE PHILIPS N.V., Eindhoven (NL)

(72) Inventors: Bernard Joseph Savord, Andover, MA (US); Jeffrey Daniel Sherman, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 18/998,710

(22) PCT Filed: Jul. 18, 2023

(86) PCT No.: PCT/EP2023/069844
§ 371 (c)(1),
(2) Date: Jan. 27, 2025

(87) PCT Pub. No.: WO2024/022879
PCT Pub. Date: Feb. 1, 2024

(65) Prior Publication Data
US 2026/0041399 A1     Feb. 12, 2026

Related U.S. Application Data

(60) Provisional application No. 63/392,902, filed on Jul. 28, 2022.

(30) Foreign Application Priority Data

Aug. 4, 2022    (EP) ..................................... 22188751

(51) Int. Cl.
*A61B 8/00*         (2006.01)
*A61B 8/14*         (2006.01)
(Continued)

(52) U.S. Cl.
CPC .............. *A61B 8/4488* (2013.01); *A61B 8/14* (2013.01); *A61B 8/54* (2013.01); *A61B 8/56* (2013.01);
(Continued)

(58) Field of Classification Search
CPC ........... A61B 8/4488; A61B 8/14; A61B 8/54; A61B 8/56; G01S 7/52057; G01S 15/8927
See application file for complete search history.

(56) References Cited

U.S. PATENT DOCUMENTS

| | | |
|---|---|---|
| 5,123,415 A | 6/1992 | Daigle |
| 5,462,057 A | 10/1995 | Hunt et al. |

(Continued)

FOREIGN PATENT DOCUMENTS

| | | |
|---|---|---|
| WO | 2017149421 A1 | 9/2017 |
| WO | 2022069264 A1 | 4/2022 |

OTHER PUBLICATIONS

International Search Report and Written Opinion for PCT/EP2023/069844; Mailing date: Oct. 5, 2023, 13 pages.

*Primary Examiner* — Joel Lamprecht

(57) ABSTRACT

A system and method are provided for controlling an ultrasound probe having a transducer array of transducer elements. The method includes receiving echo signals at the transducer elements reflected in near and/or far fields of a medium, and outputting electrical echo signals; digitizing the electrical echo signals; multiplexing the digitized echo signals to output a first set of the digitized echo signals corresponding to a first set of transducer elements of the plurality of transducer elements defining a small aperture for receiving the echo signals reflected in the near field; grouping transducer elements of a second set of transducer elements into sub-arrays providing a second set of digitized echo signals; summing together the digitized echo signals (Continued)

from the second set of the transducer elements within each sub-array for receiving echo signals reflected in the far field, wherein the second set of transducer elements contains more transducer elements than the first set of the transducer elements; and outputting an echo data stream including the first and/or second sets of the digitized echo signals to a host system via a communication interface having a fixed maximum bandwidth.

16 Claims, 7 Drawing Sheets

(51) Int. Cl.
  *G01S 7/52*    (2006.01)
  *G01S 15/89*    (2006.01)
(52) U.S. Cl.
  CPC ...... *G01S 7/52057* (2013.01); *G01S 15/8927*
                (2013.01)

(56)       References Cited

U.S. PATENT DOCUMENTS

| | | |
|---|---|---|
| 6,183,419 B1 | 2/2001 | Wildes |
| 12,345,810 B2 * | 7/2025 | Savord ................ G01S 7/52033 |
| 2008/0114248 A1 | 5/2008 | Urbano et al. |
| 2021/0007717 A1 | 1/2021 | Savord |

* cited by examiner

ULTRASOUND IMAGING SYSTEM INCLUDING CONFIGURABLE TRANSDUCER PROBE

CROSS-REFERENCE TO PRIOR APPLICATIONS

This application is the U.S. National Phase application under 35 U.S.C. § 371 of International Application No. PCT/EP2023/069844, filed on Jul. 18, 2023, which claims the benefit of U.S. Provisional Patent Application No. 63/392,902, filed on Jul. 28, 2022, and European Patent Application No. 22188751.6, filed on Aug. 4, 2022. These applications are hereby incorporated by reference herein.

BACKGROUND OF THE INVENTION

Ultrasound imaging has become indispensable for many medical imaging applications. An ultrasound imaging system typically includes an ultrasound probe and a processing system. The probe may include an array of ultrasound transducer elements configured to emit acoustic waves through a patient's body and to receive echo signals as the acoustic waves are reflected from the tissues, organs and other structures. The timing and strength of the echo signals generally correspond to the size, shape, and mass of the structures in the patient's body, images of which are displayed to a user of the ultrasound imaging system.

Modern ultrasound imaging systems may include digital probes that digitize the echo signals from the transducer elements within the probes themselves. Since analog processing channels are not required in the base system connected to digital probes, image quality is not constrained by the ultrasound imaging system. However, the digital probes have fixed digital bandwidths that limit the performance of the ultrasound imaging system. That is, the maximum data rate achievable in a digital probe is limited by power (heat), transistor technology speed (which is a trade-off with regard to cost and reliability), and the number of lines in a cable assembly connecting the digital probe to a host system. When these metrics are defined by project requirements, various methods must be used to reduce resulting data rates to accommodate a desired number of channels or dynamic range.

What is needed is an ultrasound imaging system with a digital probe that efficiently reduces data rates of received echo signals, thereby effectively increasing bandwidth. Reducing data rates would allow for more channels to be recorded without impacting final image quality, while avoiding using more power, implementing faster/more expensive technologies, and/or adding more conductors.

WO 2022/069264 A1 describes an ultrasound imaging system including an ultrasound probe. The ultrasound probe includes a housing and a transducer array with first, second, and third acoustic elements.

US 2008/114248 A1 describes a method for conducting ultrasound interrogation of a medium including transmitting a non-beamformed or beamformed ultrasound wave into a medium.

SUMMARY OF THE INVENTION

According to a representative embodiment, a transducer probe of an ultrasound imaging system includes a transducer array, multiple analog to digital converters (ADCs), a combiner, a switch, a digital processing unit, and a communication interface. The transducer array includes multiple transducer elements configured to emit ultrasound signals into a medium, to receive echo signals responsive to the ultrasound signals being reflected in a near field and a far field of the medium, and to output corresponding electrical echo signals. The ADCs are configured to digitize the electrical echo signals to provide digitized echo signals. The combiner comprises a multiplexer and a beamformer. The multiplexer is configured to multiplex the digitized echo signals to output a first set of the digitized echo signals corresponding to a first set of transducer elements of the plurality of transducer elements defining a small aperture for receiving the echo signals reflected in the near field. The beamformer comprises a plurality of adders configured to group transducer elements of a second set of transducer elements into sub-arrays providing a second set of digitized echo signals, and to sum together the digitized echo signals from the second set of the transducer elements within each sub-array for receiving the echo signals reflected in the far field, wherein the second set of the transducer elements contains more transducer elements than the first set of the transducer elements. The switch is operable to select the multiplexer for near field ultrasound imaging and the beamformer for far field ultrasound imaging. The digital processing unit is configured to receive the first set of the digitized echo signals and the second set of the digitized echo signals, and to output a corresponding digital echo stream. The communication interface is configured to communicate the echo data stream to an ultrasound imaging system host, where the communication interface has a fixed maximum bandwidth. The small aperture defined by the first set of transducer elements provides a digital bandwidth of the echo data stream that is less than the maximum bandwidth of the communication interface.

In some embodiments, the combiner may further comprise a sampling rate switch configured to selectively connect the plurality of ADCs to a first signal generator or a second signal generator, wherein the first signal generator is configured to provide a first signal that controls the plurality of ADCs to sample the electrical echo signals at a first sampling rate for near field imaging, and to provide a second signal that controls the plurality of ADCs to sample the electrical echo signals at a second sampling rate for far field imaging, and wherein the first sampling rate is greater than the second sampling rate.

According to another representative embodiment, a method is provided for controlling an ultrasound transducer probe including a transducer array having multiple transducer elements. The method includes receiving echo signals at the multiple transducer elements responsive to ultrasound signals emitted by at least some transducer elements of the multiple transducer elements, where the echo signals are reflected in a near field and a far field of the medium, and outputting corresponding electrical echo signals; digitizing the electrical echo signals to provide digitized echo signals; multiplexing the digitized echo signals to output a first set of the digitized echo signals corresponding to a first set of transducer elements of the plurality of transducer elements defining a small aperture for receiving the echo signals reflected in the near field; grouping transducer elements of a second set of transducer elements into sub-arrays providing a second set of digitized echo signals; summing together the digitized echo signals from the second set of the transducer elements within each sub-array for receiving echo signals reflected in the far field, wherein the second set of transducer elements contains more transducer elements than the first set of the transducer elements; and outputting an echo data stream including the first set and the second set of the digitized echo signals to a host system via a communication interface having a fixed maximum bandwidth, where the small aperture defined by the first set of transducer elements provides a digital bandwidth of the echo data stream that is less than the maximum bandwidth of the communication interface.

According to another aspect of the present invention, a transducer probe of an ultrasound imaging system includes a transducer array, multiple analog to digital converters (ADCs), a combiner, a digital processing unit, and a communication interface. The transducer array includes multiple transducer elements configured to emit ultrasound signals into a medium, to receive echo signals responsive to the ultrasound signals being reflected in a near field and/or a far field of the medium, and to output corresponding electrical echo signals. The ADCs are configured to digitize the electrical echo signals to provide digitized echo signals. The combiner is configured to process a first set of the digitized echo signals corresponding to a first set of transducer elements of the multiple transducer elements differently than a second set of the digitized echo signals corresponding to a second set of transducer elements of the multiple transducer elements, where the first set of transducer elements contains fewer transducer elements than the multiple transducer elements for receiving the echo signals reflected in the near field, thereby defining a small aperture, and where the second set of transducer elements contains more transducer elements than the first set of transducer elements for receiving the echo signals reflected in the far field, thereby defining a large aperture. The digital processing unit is configured to receive the first set of the digitized echo signals and/or the second set of the digitized echo signals, and to output a corresponding digital echo stream. The communication interface is configured to communicate the echo data stream to an ultrasound imaging system host, where the communication interface has a fixed maximum bandwidth. The small aperture defined by the first set of transducer elements provides a digital bandwidth of the echo data stream that is less than the maximum bandwidth of the communication interface.

In some embodiments, the combiner may comprise a multiplexer configured to multiplex the digitized echo signals to output the first set of the digitized echo signals corresponding to the first set of the transducer elements defining the small aperture.

In some embodiments, the electrical echo signals may be digitized at a first sampling rate to provide the first set of the digitized echo signals and the electrical echo signals are digitized at a second sampling rate to provide the second set of the digitized echo signals, wherein the first sampling rate is different than the second sampling rate, wherein preferably the first sampling rate is at least 25 percent greater than the second sampling rate.

In some embodiments, the combiner may comprise a plurality of adders configured to group the transducer elements of the second set of transducer elements into sub arrays, and to sum together the digitized echo signals from the transducer elements within each sub array.

In some embodiments, each sub-array may contain two of the transducer elements of the second set of transducer elements.

In some embodiments, the combiner may further comprise a plurality of delay elements arranged prior to plurality of adders, and configured to delay the digitized echo signals by respective delay amounts in order to focus the digitized echo signals at respective pixels being imaged.

According to another aspect of the present invention, a method is provided for controlling an ultrasound transducer probe including a transducer array having multiple transducer elements. The method includes receiving echo signals at the multiple transducer elements responsive to ultrasound signals emitted by at least some transducer elements of the multiple transducer elements, where the echo signals are reflected in a near field and/or a far field of the medium, and outputting corresponding electrical echo signals; digitizing the electrical echo signals to provide digitized echo signals; selecting a first set of the digitized echo signals corresponding to a first set of transducer elements of the plurality of transducer elements, where the first set of transducer elements contains fewer transducer elements than the multiple transducer elements for receiving the echo signals reflected in the near field, thereby defining a small aperture; selecting a second set of the digitized echo signals corresponding to a second set of transducer elements of the multiple transducer elements, where the second set of transducer elements contains more transducer elements than the first set of transducer elements for receiving the echo signals reflected in the far field, thereby defining a large aperture; and outputting an echo data stream including the first set and/or the second set of the digitized echo signals to a host system via a communication interface having a fixed maximum bandwidth, where the small aperture defined by the first set of transducer elements provides a digital bandwidth of the echo data stream that is less than the maximum bandwidth of the communication interface.

In some embodiments, the electrical echo signals may be digitized at a first sampling rate to provide the first set of the digitized echo signals and the electrical echo signals are digitized at a second sampling rate to provide the second set of the digitized echo signals, wherein the first sampling rate is different than the second sampling rate, wherein preferably the first sampling rate is at least 25 percent greater than the second sampling rate.

In some embodiments, selecting the first set of the digitized echo signals may comprise multiplexing the digitized echo signals to output the first set of the digitized echo signals corresponding to the first set of transducer elements.

In some embodiments, selecting the second set of the digitized echo signals comprises grouping the transducer elements of the second set of transducer elements into sub arrays; and summing the digitized echo signals from the transducer elements within each sub array to reduce a digital bandwidth of the second set of the digitized echo signals.

In some embodiments, each sub-array may contain two of the transducer elements of the second set of transducer elements.

In some embodiments, selecting the first set of digitized echo signals may further comprise prior to summing the digitized echo signals from the transducer elements within each sub-array, delaying the digitized echo signals by respective delay amounts in order to focus the digitized echo signals at respective pixels being imaged.

BRIEF DESCRIPTION OF THE DRAWINGS

The representative embodiments are best understood from the following detailed description when read with the accompanying drawing figures. It is emphasized that the various features are not necessarily drawn to scale. In fact, the dimensions may be arbitrarily increased or decreased for clarity of discussion. Wherever applicable and practical, like reference numerals refer to like elements.

DETAILED DESCRIPTION OF EMBODIMENTS

In the following detailed description, for the purposes of explanation and not limitation, representative embodiments disclosing specific details are set forth in order to provide a thorough understanding of an embodiment according to the present teachings. Descriptions of known systems, devices, materials, methods of operation and methods of manufacture may be omitted so as to avoid obscuring the description of the representative embodiments. Nonetheless, systems, devices, materials and methods that are within the purview of one of ordinary skill in the art are within the scope of the present teachings and may be used in accordance with the representative embodiments. It is to be understood that the terminology used herein is for purposes of describing particular embodiments only and is not intended to be limiting. The defined terms are in addition to the technical and scientific meanings of the defined terms as commonly understood and accepted in the technical field of the present teachings.

It will be understood that, although the terms first, second, third, etc. may be used herein to describe various elements or components, these elements or components should not be limited by these terms. These terms are only used to distinguish one element or component from another element or component. Thus, a first element or component discussed below could be termed a second element or component without departing from the teachings of the inventive concept.

The terminology used herein is for purposes of describing particular embodiments only and is not intended to be limiting. As used in the specification and appended claims, the singular forms of terms "a," "an" and "the" are intended to include both singular and plural forms, unless the context clearly dictates otherwise. Additionally, the terms "comprises," "comprising," and/or similar terms specify the presence of stated features, elements, and/or components, but do not preclude the presence or addition of one or more other features, elements, components, and/or groups thereof. As used herein, the term "and/or" includes any and all combinations of one or more of the associated listed items.

As used in the specification and appended claims, and in addition to their ordinary meanings, the term "approximately" mean to with acceptable limits or degree. For example, "approximately 20 GHz" means one of ordinary skill in the art would consider the signal to be 20 GHz within reasonable measure.

As used in the specification and appended claims, in addition to their ordinary meanings, the term "substantially" means within acceptable limits or degree. For example, the "plurality of transducer ports are substantially the same" means one of ordinary skill in the art would consider the plurality of transducer ports to be the same.

Figure 1:
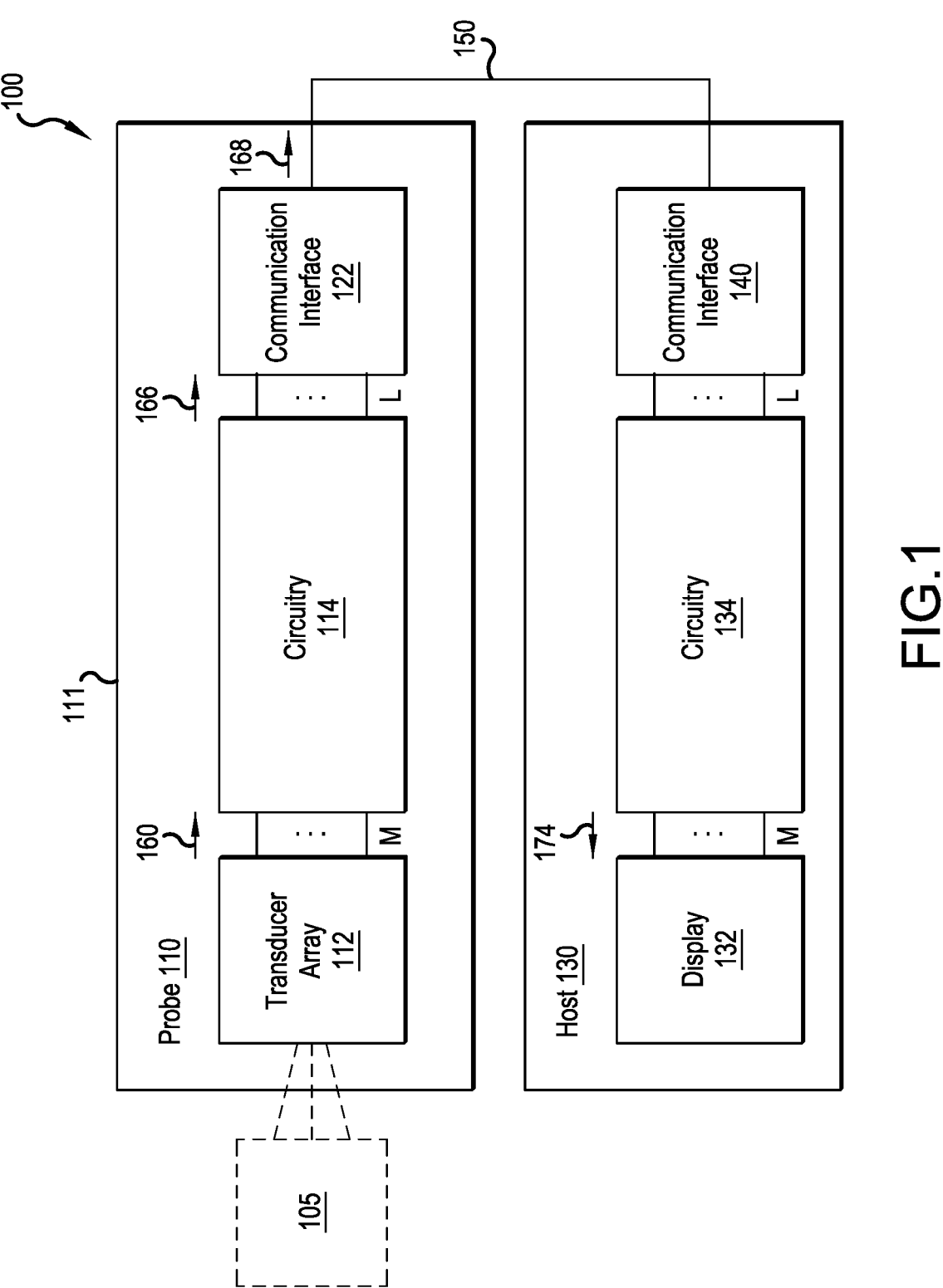
FIG. 1 is a simplified schematic diagram of an ultrasound imaging system including an ultrasound probe and a host, according to a representative embodiment.

FIG. 1 is a simplified schematic diagram of an ultrasound imaging system including an ultrasound probe and a host, according to a representative embodiment. The system is used for scanning a region, arca, or volume of a patient's body. Portions of the system are described, for example, in U.S. Patent App. Pub. No. 2021/0007717, titled "DIGITAL ULTRASOUND CABLE AND ASSOCIATED DEVICES, SYSTEMS, AND METHODS," filed Jan. 31, 2019, which is hereby incorporated by reference in its entirety.

Referring to FIG. 1, ultrasound imaging system 100 includes a digital ultrasound probe 110 in communication with an ultrasound host system 130 over a communication link 150. At a high level, the probe 110 emits ultrasound waves towards an object 105 (e.g., a patient's body or anatomical structure) and receives ultrasound echoes that are reflected from the object 105. The probe 110 digitizes electrical echo signals representative of the received echoes, and transmits the digitized signals as a digital echo data stream over the communication link 150 to the host system 130 for processing and image display. The communication link 150 is able to communicate data in analog format, digital format, and/or both analog and digital formats. The probe 110 may be in any suitable form for imaging various body parts of a patient while positioned inside or outside of the patient's body. For example, the probe 110 may be in the form of a handheld ultrasound scanner, such as a transthoracic echocardiography (TTE) probe, or a patch-based ultrasound device. In some embodiments, the probe 110 is not handheld, but rather is held in place via a strap, mechanical holder, and/or adhesive. In some embodiments, the probe 110 can be a catheter, a transesophageal echocardiography (TEE) probe, or other an endo-cavity or intraluminal probe. The probe 110 may include any of the components shown in FIG. 1. Any of the components of the probe 110 may be positioned or stored in a housing 111. When the probe 110 is a handheld probe, the housing 111 is configured to be grasped by the hand of a user (e.g., sonographer).

In the depicted configuration, the probe 110 includes a transducer array 112, the circuitry 114, and a communication interface 140 within the housing 111. The transducer array 112 emits ultrasound signals (waves) towards the object 105 and receives echo signals (waves) reflected from the interior of the object 105 back to the transducer array 112. The transducer array 112 may include an array of acoustic elements. The transducer array 112 may be coupled to a microbeamformer (not shown), and controls reception of signals by the acoustic elements. In exemplary embodiments, the transducer array 112 is a 1. X-dimensional array, such as a 1.25D array or a 1.5D array, for example. In other embodiments, the transducer array may be arranged in a one-dimensional (1D) array or in a two-dimensional (2D) array.

The acoustic elements may be referred to as transducer elements, discussed below, and may be capacitive micromachined ultrasonic transducers (CMUTs) or piezoelectric transducers formed of materials such as PZT or PVDF, for example. Each transducer element may emit ultrasound signals into the object 105 and may receive echo signals as the ultrasound signals are reflected from within the object 105. Each transducer element generates an analog electrical signal representative of the received ultrasound echo signals. The transducer array 112 may include M transducer elements arranged in row(s) and column(s) producing M analog ultrasound echo signals.

Circuitry 114 positioned within the probe 110 may be of any suitable type of circuitry and may serve several functions. For example, the circuitry 114 may include resistors, capacitors, transistors, inductors, relays, clocks, timers, or any other suitable electrical component that may be integrated in an integrated circuit. In addition, the circuitry 114 may be configured to support analog signals and/or digital signals transmitted to or from the transducer array 112 and/or the probe 110. In some embodiments, the circuitry 114 may include analog frontends (AFEs), analog-to-digital converters (ADCs), multiplexers (MUXs), and encoders, among various other components. In some embodiments, the circuitry 114 may include hardware components, software components, and/or a combination of hardware components and software components. Examples of the circuitry 114 are discussed below with reference to FIGS. 4 and 5.

The communication interface 122 is coupled to the circuitry 114 via L signal lines. In some embodiments, the circuitry 114 may reduce the number of required lines from M signal lines to L signal lines. This may be accomplished by any suitable method using any suitable component. For example. MUXs, beamformers, or other components may be used to reduce the M signal lines from the transducer array 112 to L signal lines 166, as discussed below. In the embodiment of FIG. 1. L is less than M. The communication interface 122 is configured to transmit the L signals to the host system 130 via the communication link 150. In an embodiment, the communication interface 122 and/or the communication link 150 has a fixed maximum bandwidth. The communication interface 122 may include a combination of hardware components and software components configured to generate signals 168 carrying the information from the L signals transmission over the communication link 150. In an exemplary embodiment, the signals 168 are digital signals such that digital ultrasound data is transmitted from the probe 110 to the host system 130, as discussed below. The communication link 150 may include L data lanes for transferring the signals 168 to the host system 130.

The host system 130 may be any suitable computing and display device, such as a workstation, a personal computer (PC), a laptop, a tablet, a mobile phone, or a patient monitor. In some embodiments, the host system 130 may be located on a moveable cart. The host system 130 includes a communication interface 140 configured to receive the signals 168 from the communication link 150. The communication interface 140 may include hardware components, software components, or a combination of hardware components and software components. The communication interface may be substantially similar to the communication interface 122 in the probe 110.

Circuitry 134 positioned within the host system 130 may be of any suitable type and may serve any suitable function. For example, the circuitry 134 may include resistors, capacitors, transistors, inductors, relays, clocks, timers, processing components, memory components, or any other suitable electrical component that may be integrated in an integrated circuit. In addition, the circuitry 134 may be configured to support analog signals and/or digital signals transmitted to or from the probe 110. The circuitry 134 may be configured to process the digital signals 168 received from the probe 110. For example, the circuitry 134 may expand L signal lines received from the probe 110 to the original M signal lines corresponding to the specific transducer elements or groups or patches of transducer elements within the transducer array 112. The circuitry 134 may be configured to generate image signals 174 for display to a user and/or perform image processing and image analysis for various diagnostic modalities or ultrasound types (B mode. CW Doppler, etc.). The circuitry 134 may additionally include one or more processing circuits, discussed below with reference to FIG. 2. For example, the circuitry 134 may include a general purpose computer, a computer processor, a microprocessor, a graphics processing unit (GPU), a central processing unit (CPU), a digital signal processor (DSP), a microcontroller, a state machine, programmable logic device, field programmable gate arrays (FPGAs), application specific integrated circuits (ASICs), systems on a chip (SOC), or combinations thereof. The circuitry 134 may be configured to generate image signals 174 for display to a user and/or perform image processing and image analysis for various diagnostic modalities.

The display 132 is coupled to the circuitry 134. The display 132 may include a monitor, a touch-screen, a television, a liquid crystal display (LCD), a light emitting diode (LED) display, a flat panel display, a solid-state display, a cathode ray tube (CRT) display, or any suitable display, for example. The display 132 is configured to display images and/or diagnostic results processed by the circuitry 134.

The host system 130 may further include a user interface (not shown) for providing information and data output by the circuitry 134 to the user and/or for receiving information and data input by the user. The user interface may include a mouse, a keyboard, a mouse, a trackball, a joystick, a microphone, a video camera, a touchpad, a touchscreen, voice or gesture recognition captured by a microphone or video camera, for example. All or part of the interface may be incorporated with the display 132 as a graphical user interface (GUI) for displaying and receiving information to and from the user.

While FIG. 1 is described in the context of transferring detected ultrasound echo signal data from the probe 110 to the host system 130 for display, the host system 130 may also generate and transmit control signals for controlling operation the probe 110, for example, the excitations of the transducer elements at the transducer array 112.

Figure 2:
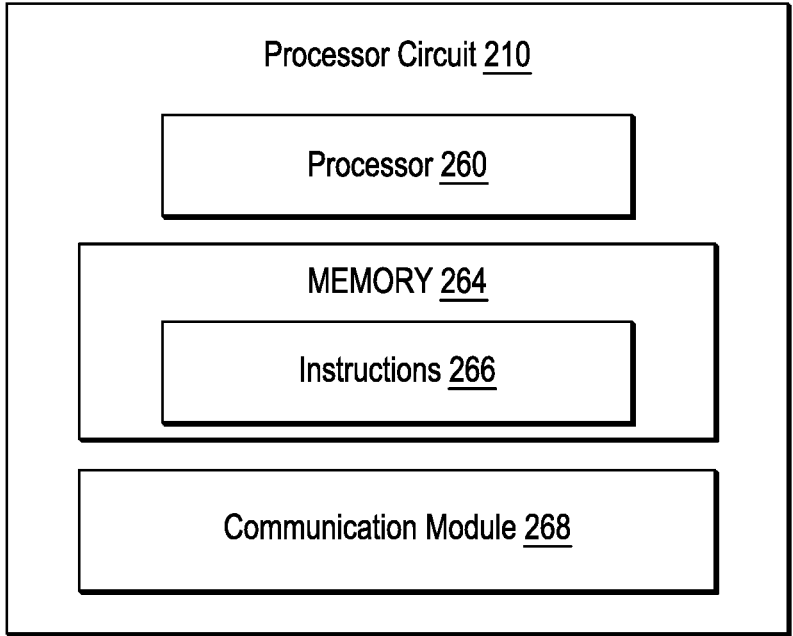
FIG. 2 is a simplified schematic diagram of an illustrative processor circuit implemented by the ultrasound imaging system, according to a representative embodiment.

FIG. 2 is a simplified schematic diagram of a processor circuit implemented by the ultrasound imaging system 100, according to a representative embodiment. For example, the processor circuit 210 may be implemented in the probe 110, the host system 130 of FIG. 1, and/or any other suitable location. One or more processor circuits 210 may be configured to carry out the operations described herein. The processor circuit 210 may be part of the circuitry 114 and/or the circuitry 134, or may be separate circuitry. In an example, the processor circuit 210 may be in communication with the transducer array 112, the circuitry 114, communication interface 122, communication interface 140, the circuitry 134, and/or the display 132, as well as any other suitable component or circuit within ultrasound imaging system 100.

Referring to FIG. 2, the processor circuit 210 includes a processor 260, memory 264, and a communication module 268. These elements may be in direct or indirect communication with each other, for example via one or more buses.

The processor 260 may be implemented by a general purpose computer, a computer processor, a microprocessor, a GPU, a CPU, a DSP, a microcontroller, a state machine, programmable logic device, FPGAs, ASICs, SOCs, or combinations thereof, using any combination of hardware, software, firmware, hard-wired logic circuits, or combinations thereof. Additionally, any processing unit or processor herein may include multiple processors, parallel processors, or both. Multiple processors may be included in, or coupled to, a single device or multiple devices.

The term "processor" as used herein encompasses an electronic component able to execute a program or machine executable instruction. References to a computing device comprising "a processor" should be interpreted to include more than one processor or processing core, as in a multi-core processor. A processor may also refer to a collection of processors within a single computer system or distributed among multiple computer systems, such as in a cloud-based or other multi-site application. The term computing device should also be interpreted to include a collection or network of computing devices each including a processor or processors. Programs have software instructions performed by one or multiple processors that may be within the same computing device or which may be distributed across multiple computing devices.

The memory 264 stores instructions executable by the processor 260. The memory 264 may include a main memory and/or a static memory, where such memories may communicate with each other and the processor 260 via one or more buses. The memory 264 stores instructions used to implement some or all aspects of methods and processes described herein. The memory 264 may include a cache memory (e.g., a cache memory of the processor 260), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory.

The memory 264 includes a non-transitory computer-readable medium that stores instructions 266. The instructions 266 may include instructions that, when executed by the processor 260, cause the processor 260 to perform the operations described herein with reference to the probe 110 and/or the host system 130. The instructions 266 may also be referred to as code. The terms "instructions" and "code" should be interpreted broadly to include any type of computer-readable statement(s). For example, the terms "instructions" and "code" may refer to one or more programs, routines, sub-routines, functions, procedures, etc. "Instructions" and "code" may include a single computer-readable statement or many computer-readable statements. As used herein, the term "non-transitory" is to be interpreted not as an eternal characteristic of a state, but as a characteristic of a state that will last for a period. The term "non-transitory" specifically disavows fleeting characteristics such as characteristics of a carrier wave or signal or other forms that exist only transitorily in any place at any time. The memory 264 may be secure and/or encrypted, or unsecure and/or unencrypted.

The communication module 268 may include any electronic circuitry and/or logic circuitry to facilitate direct or indirect communication of data between the processor circuit 210, the probe 110, and/or the display 132. In that regard, the communication module 268 may be an input/output (I/O) device. In some instances, the communication module 268 facilitates direct or indirect communication between various elements of the processor circuit 210 and/or the probe 110 and/or the host system 130.

Figure 3:
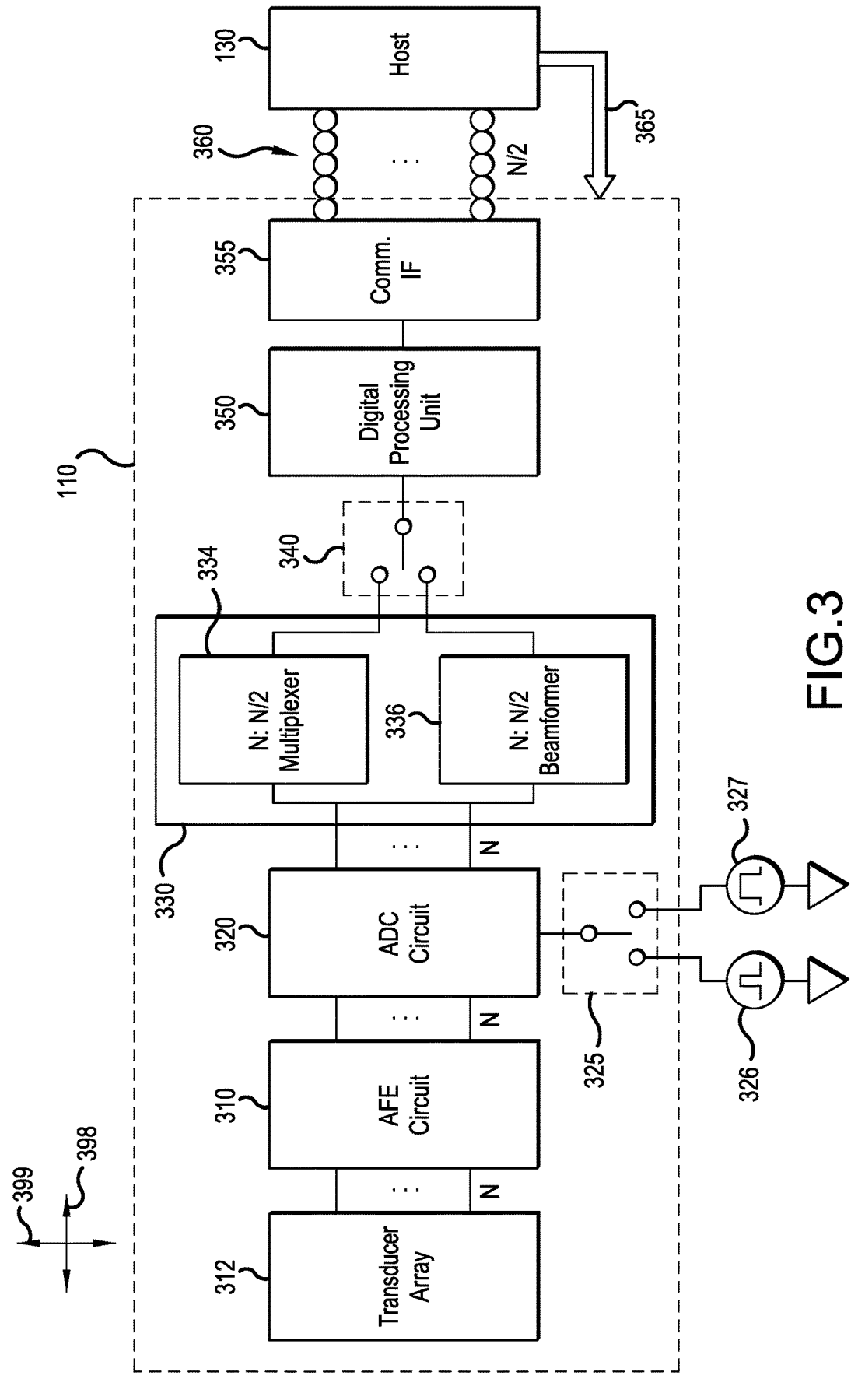
FIG. 3 is a schematic diagram illustrating illustrative circuitry of an ultrasound imaging system with a transducer array, according to a representative embodiment.

FIG. 3 is a schematic diagram showing illustrative circuitry of an ultrasound imaging system 100 with a transducer array, according to a representative embodiment. In particular, FIG. 3 provides a more detailed view of circuitry within the probe 110 connected to the host system 130, according to a representative embodiment. Any of the components of the probe 110 may be positioned or arranged in a housing (e.g., housing 111).

Referring to FIG. 3, the circuitry of the probe 110 includes the transducer array 312, which may be substantially the same as the transducer array 112, discussed above. The transducer array 312 is in communication with analog front-end (AFE) circuit 310 and digitization circuit 320 via corresponding conductors. The conductors may include conductive pathways or conductive traces positioned on a printed circuit board (PCB), a flexible or inflexible substrate, or in any other suitable configuration. Axes 398 and 399 provide orientation directions of the transducer array 312, where the axis 398 illustrates the elevational or elevation direction and the axis 399 illustrates the azimuthal or lateral direction. For ease of explanation, the transducer array 312 is assumed to be a 1.0-dimensional (D) array having a single row of N transducer elements in the azimuthal direction, as discussed below. Any suitable number N of transducer elements may be included, without departing from the scope of the present teachings. For example, the row N transducer elements include 2, 8, 16, 50, 64, 80, 90, 100, etc., transducer elements. The N transducer elements have N associated channels (signal paths) for communicating analog and digital signals.

A transmit portion of the transducer elements are configured to emit ultrasound signals into a medium (e.g., object 105). A receive portion of the N transducer elements are configured to receive ultrasound echo signals in responsive to the emitted ultrasound signals being reflected from the medium and to output corresponding electrical echo signals. Each of the transmit portion and the receive portion may include one or more of the transducer elements of the transducer array 312 (up to and including all N of the transducer elements), and may include the same or different transducers, in order to provide unique benefits for any particular situation or to meet application specific design requirements of various implementations, as would be apparent to one skilled in the art.

In various embodiments, the transducer array 312 suitable type of 1. XD array, such as a 1.25D array. 1.5D array, or 1.75D array, for example, or 2. XD array. In some aspects, a 1.25D array may include circuitry for controlling the aperture size in elevation. A 1.5D array may include additional circuitry configured to apply various delays to received signals from elements in the elevation dimension so as to focus these signals. In some embodiments. 1.25D and 1.5D arrays may assume symmetry where gain and delay are symmetric about the center of the elevation dimension. A 1.75D array may apply different delays to each of the outer transducer elements in elevation and may be configured to steer the acoustic beam. 1.75D arrays may be symmetrical about a center row of elements or may be asymmetrical.

The AFE circuit 310 is configured to perform signal processing on the electrical echo signals output by the transducer elements of the transducer array 312. For example, the AFE circuit 310 may include N gain controllers in the channels corresponding to the N transducer elements, respectively, for adjusting gain of the electrical echo signals. The gain controllers may be time gain compensation (TGC) controllers or automatic gain control (AGC) controllers, for example. The AFE circuit 310 may include additional analog signal conditioning circuitry, such as filters, operational amplifiers, and the like, as would be apparent to one skilled in the art.

The digitization circuit 320 is configured to digitize the conditioned electrical echo signals output by the AFE circuit 310. The digitization circuit 320 may include N ADCs in the channels corresponding to the N transducer elements, respectively, for digitizing the electrical echo signals output by the N gain controllers. The ADCs output N digital echo signals, respectively. The output of each of the ADCs may be a 12-bit digital signal, for example, although the ADCs may have any suitable bitrate (e.g., 4-bit, 8-bit, 16-bit, 24-bit, 32-bit, 64-bit).

In an embodiment, the ADCs of the digitization circuit 320 have adjustable sampling rates, where a sampling rate for digitizing electrical echo signals from the near field (first sampling rate) is higher than a sampling rate for digitizing electrical echo signals from the far field (second sampling rate). That is, higher sampling rates are used for ultrasound imaging at smaller depths within a medium (e.g., an anatomy of a patient), while lower sampling rates are used for ultrasound imaging at larger depths within the medium. This is because the ultrasound echo signals reflected from the near field have higher frequencies having passed through less high frequency attenuating tissue than the ultrasound signals reflected from the far field. In some cases, the system uses a higher frequency transmit excitation in the near field further accentuating the high frequency nature of the near field data. For example, the near field sampling rate of the ADCs may be twice the far field sampling rate. Generally, the near field sampling rate is at least 25 percent greater than the far field sampling rate. The different sampling rates may be selected using representative sampling rate switch 325, which may be controlled, e.g., by processor 260, to switch between near field signal generator 326 and a far field signal generator 327. The near field signal generator 326 provides a first signal that controls the ADCs to sample the electrical echo signals at the first sampling rate for near field imaging, and the far field signal generator 327 provides a second signal that controls the ADCs to sample the electrical echo signals at the second sampling rate for far field imaging.

The probe 110 includes a combiner 330 and a near field/far field switch 340 operable. e.g., by the processor 260, for selecting near field or far field operations. The combiner 330 is configured to reduce the total number of channels from the digitizing circuit 320, thereby reducing the data rate and thus digital bandwidth for transmitting data to the host system 130. In the depicted embodiment, the combiner 330 includes a multiplexer 334 for selecting digitized echo signals for near field ultrasound imaging and a beamformer 336 for beamforming sub-arrays of digitized echo signals for far field ultrasound imaging. The near field/far field switch 340 is operable to select either the multiplexer 334 or the beamformer 336 in accordance with the near field or far field ultrasound imaging, respectively.

As discussed further below with reference to FIG. 4, the multiplexer 334 is configured to multiplex the digitized echo signals corresponding to echo signals reflected from the near field in order to reduce the number of digitized echo signals. For example, in the depicted embodiment, the multiplexer 334 is an N:N/2 multiplexer, which selects half of the digital echo signals from half of the transducer elements in the azimuthal direction indicated by axis 399, respectively. The combiner 330 therefore reduces the number of channels from N channels to N/2 channels. The transducer elements that provide the selected digital echo signals may be referred to as a first set of transducer elements, which contains fewer than all of the N transducer elements in the transducer array 312. The first set of transducer elements thereby defines a small aperture for receiving the echo signals. The first set of transducer elements may have various arrangements relative to one another to provide different apertures within the transducer array 212. For example, the transducer elements may be adjacent to one another and grouped centered about the image line being acquired to provide an aperture for receiving the echo signals reflected from the near field. Other arrangements of the first set of transducer elements may be implemented in order to provide unique benefits for any particular situation or to meet application specific design requirements of various implementations, as would be apparent to one skilled in the art.

As discussed further below with reference to FIG. 5, the beamformer 336 includes adders configured to sum together signals in the azimuthal direction indicated by axis 399 from the digitizing circuit 320 into sub-arrays, so that there are fewer digitized echo signals than those provided by all of the transducer elements in the transducer array 316. The transducer elements that provide the digital echo signals to be combined may be referred to as a second set of transducer elements. For example, the beamformer 336 may be an N:N/2 beamformer, which combines pairs of digital echo signals. In this case, each sub-array contains two transducer elements of the transducer array 316. The beamformer 336 may further include delay elements arranged prior to the adders in order to delay the signals by respective delay amounts in order to focus the signals at respective pixels being imaged. The beamformer 336 may be considered a digital beamformer that performs a second stage of beam-forming (delaying and summing of signals) after a first stage of beamforming is completed by an optional analog beam-former (not shown). In the depicted embodiment, the com-biner 330 reduces the number of channels from N channels to N/2 channels. Sub-arrays combining different numbers of digital echo signals may be implemented in order to provide unique benefits for any particular situation or to meet application specific design requirements of various imple-mentations, as would be apparent to one skilled in the art.

The probe 110 further includes a digital processing unit 350, which may include a serializer and a high speed current mode logic (CML) cable driver, in communication with combiner 330 via the near field/far field switch 340. The digital processing unit 350 may be implemented using one or more processor circuits 210, for example. The digital processing unit 350 may serialize the digitized echo signals output by the combiner 330 into high-speed serial links, and send the serialized data (e.g., B-mode data) to the host system 130 via a communication interface (not shown) and signal conductors 360. The digital processing unit 350 also may rearrange lines received from the combiner 330 and/or the digitizing circuit 320 into a high data rate, serial, digital echo data stream. In some embodiments, the digital pro-cessing unit 350 may run at a higher data rate than other circuitry within the probe 110. For example, the echo data stream may run at 2.4 GHz, whereas the other circuitry within the ultrasound channel may run at 20 MHz.

The probe 110 is connected to the host system 130 via connecting conductors, including the signal conductors 360 and power and control conductors 365. The signal conduc-tors 360 and the power and control conductors 365 may together form single cable or multiple separate cables, or may be arranged in any other suitable configuration. The signal conductors 360 and the power and control conductors 365 may be part of the communication link 150 discussed above with reference to FIG. 1.

The signal conductors 360 may correspond to a reduced number of signal lines output from the digital processing unit 350. In various embodiments, the signal conductors 360 may include only a single signal line or may include multiple signal lines. The signal conductors 360 may be twisted pairs, single conductors, coaxial conductors, or any other suitable communication pathway for transmitting data signals. In addition, in some embodiments, the signal conductors 360 may carry only digital signals. In other embodiments, the signal conductors 360 may also carry analog signals. In some embodiments, the signals may be carried over an optical link. In some embodiments, the signals may be carried wirelessly.

The power and control conductors 365 may include one or multiple signal and/or power lines including conductors, twisted pairs, or any other suitable means of transferring data, signals, or power. For example, the power and control conductors 365 may include a conductor dedicated to providing control signals or other data from the host system 130 to the probe 110. The power and control conductors 365 may further include conductors that provide necessary AC and/or DC power from the host system 130 (or other power source) to the components within the probe 110. The conductors may be in communication with a controller or any other suitable component within the host system 130, e.g., implemented by one or more processor circuits 210, and may provide signals for controlling clocks, switches, pulsers, the transducer array 312, the AFE circuit 310, the ADC circuit 320, the combiner 330, the digital processing unit 350, and/or any other component within the probe 110. In various embodiments, the power and control conductors 365 may include only a single signal line or may include multiple signal lines. The power and control conductors 365 may be twisted pairs, single conductors, coaxial conductors, or any other suitable communication pathway for transmitting data signals.

The signal conductors 360 and the power and control conductors 365 may together form one connecting cable similar to the communication link 150 described with reference to FIG. 1. Specifically, the signal conductors 360 and the power and control conductors 365 may be wrapped together with a cable shielding. The signal conductors 360, the power and control conductors 365, and any corresponding conductors enclosed together may be of any suitable length and/or may be a flexible elongate member. For example, the signal conductors 360, the power and control conductors 365, and all associated conductors may be one meter, two meters, three meters in length, or other suitable values, both larger, smaller, or therebetween. In other embodiments, the control conductors 365 and the power and control conductors 365 may form separate connecting cables of the same or varying lengths.

During an ultrasound examination, the ultrasound imaging system 100 may designate a transmit set of the transducer elements of the transducer array 316 to transmit ultrasound signals such that ultrasound energy propagates into the patient's anatomy. The ultrasound imaging system 100 may further specify a receive set of transducer elements (e.g., first or second set of transducer elements) to receive reflected ultrasound echo signals. In some embodiments, the transducer elements selected to transmit ultrasound signals may be the same transducers used to receive reflected echo signals. In other embodiments, the transducer elements used to transmit ultrasound signals may be different from the transducer elements used to receive the reflected echo signals. For example, the ultrasound imaging system 100 may select half of the transducer elements of the transducer array 316 to receive the reflected echo signals from the patient's anatomy in the near field, as discussed above.

Figure 4:
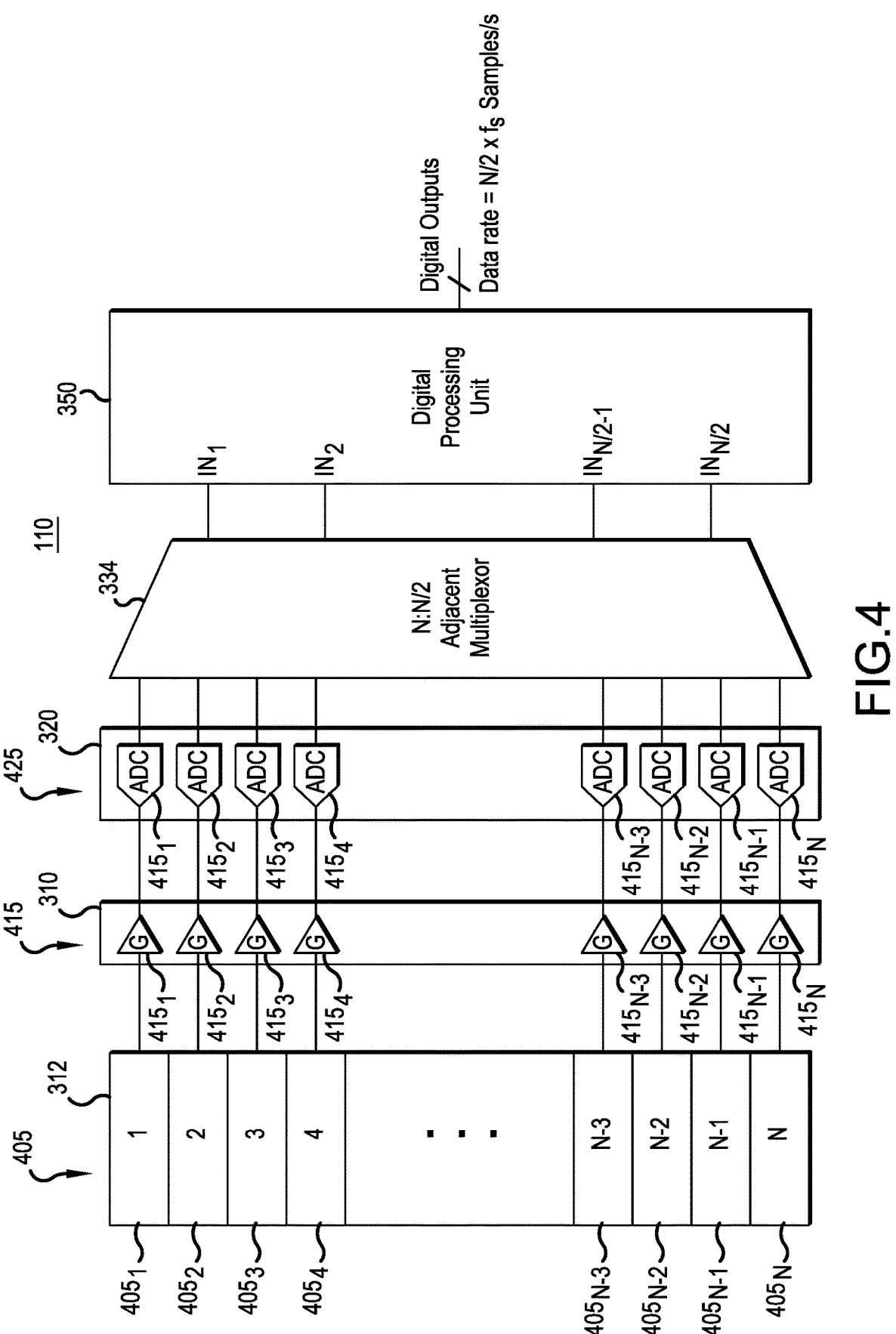
FIG. 4 is a simplified block diagram of a transducer probe in an ultrasound imaging system for reducing digital bandwidth using a multiplexer, according to a representative embodiment.

FIG. 4 is a simplified block diagram of a transducer probe in an ultrasound imaging system for reducing digital bandwidth using a multiplexer, according to a representative embodiment. The transducer probe is shown configured to receive echo signals reflected in the near field of a medium (e.g., object 105).

Referring to FIG. 4, probe 110 includes a transducer array 312, which has multiple transducer elements 405. For case of explanation, the transducer array 112 is shown as a 1.0D array having a single row of N transducer elements 405. In the depicted configuration, representative transducer elements include first transducer element $405_1$, second transducer element $405_2$, third transducer element $405_3$, fourth transducer element $405_4 . . . $, N–$3^{rd}$ transducer element $405_{N-3}$, N–$2^{nd}$ transducer element $405_{N-2}$, N–$1^{st}$ transducer element $405_{N-1}$, and N$^{th}$ transducer element $405_N$. A transmit portion of the transducer elements 405 is configured to emit ultrasound signals into a medium (e.g., object 105). A receive portion of the transducer elements 405 is configured to receive echoes from the emitted ultrasound signals being reflected within the medium and to output corresponding electrical echo signals. Each of the transmit portion and the receive portion may include one or more of the transducer elements 405 of the transducer array 412 (up to and including all of the transducer elements 405), and may include the same or different transducer elements 405, in order to provide unique benefits for any particular situation or to meet application specific design requirements of various implementations, as would be apparent to one skilled in the art.

The probe 110 further includes the AFE circuit 310, which includes at least gain controllers 415, which may be TGC controllers or AGC controllers, for example. In the depicted configuration, representative gain controllers 415 include first gain controller $415_1$, second gain controller $415_2$, third gain controller $415_3$, fourth gain controller $415_4, . . . ,$ N–$3^{rd}$ gain controller $415_{N-3}$, N–$2^{nd}$ gain controller $415_{N-2}$, N–$1^{st}$ gain controller $415_{N-1}$, and N$^{th}$ gain controller $415_N$. The gain controllers 415 are configured to adjust the gain the electrical echo signals output by transducer elements 405 in respective channels.

The probe 110 further includes the digitizing circuit 320, which includes ADCs 425 have adjustable sampling rates for sampling the analog echo signals, where the lower the sampling rate, the smaller the digital bandwidth of the digitized echo signals. In the depicted configuration, representative ADCs 425 include first ADC $425_1$, second ADC $425_2$, third ADC $425_N$, fourth ADC $425_4, . . . ,$ N–$3^{rd}$ ADC $425_{N-3}$, N–$2^{nd}$ ADC $425_{N-2}$, N–$1^{st}$ ADC $425_{N-1}$, and N$^{th}$ ADC $425_N$. The ADCs 425 are configured to digitize the electrical echo signals received from the gain controller 415 in the respective channels. Each of the ADCs 425 may have adjustable sampling rates, where the sampling rate for the near field configuration is greater than that of the far field configuration, discussed below.

The probe 110 further includes the multiplexer 334 of the combiner 330. The multiplexer 334 is configured to receive the digitized echo signals respectively output by the ADCs 425 via the respective channels, and to select some of the digitized echo signals for further processing by the digital processing unit 350. The fewer digitized echo signals selected by the multiplexer 334, the smaller the digital bandwidth of the digitized echo signals output by the multiplexer 334. For example, in the depicted embodiment, the multiplexer 334 is configured as an N:N/2 multiplexer, which reduces the number of digitized echo signals by one half. The selection of the digitized echo signals is made among channels in the azimuthal direction respectively corresponding to selected transducer elements 405, e.g., which form the small aperture for near field imaging. The selected transducer elements 405 may be referred to as the first set of transducer elements. Operation of the multiplexer 334 for selecting channels may be performed automatically, e.g., using the processor circuit 210, or manually, e.g., using a user interface or GUI.

The digital processing unit 350 is configured to receive the multiplexed digitized echo signals from the multiplexer 334, e.g., via near field/far field switch 340 (not shown), and to output a corresponding digital echo data stream that has a smaller digital bandwidth than would otherwise have been present if the digitized echo signals from all of the ADCs 425 would have been processed. When the multiplexer 334 is configured as an N:N/2 multiplexer, the data rate of the echo data stream is $N/2 \times f_s$ samples/second, where $f_s$ is the frequency of the electrical echo signals output by the transducer elements 405.

The probe 110 also includes the communication interface 355, which is configured to communicate the echo data stream from the digital processing unit 350 to the host system 130 via the signal conductors 360. Operation of the multiplexer 334 reduces the number of digital echo signals such that the digital processing unit 350 provides an echo data stream having a total digital bandwidth that is less than the fixed maximum bandwidth of the communication interface.

Figure 5:
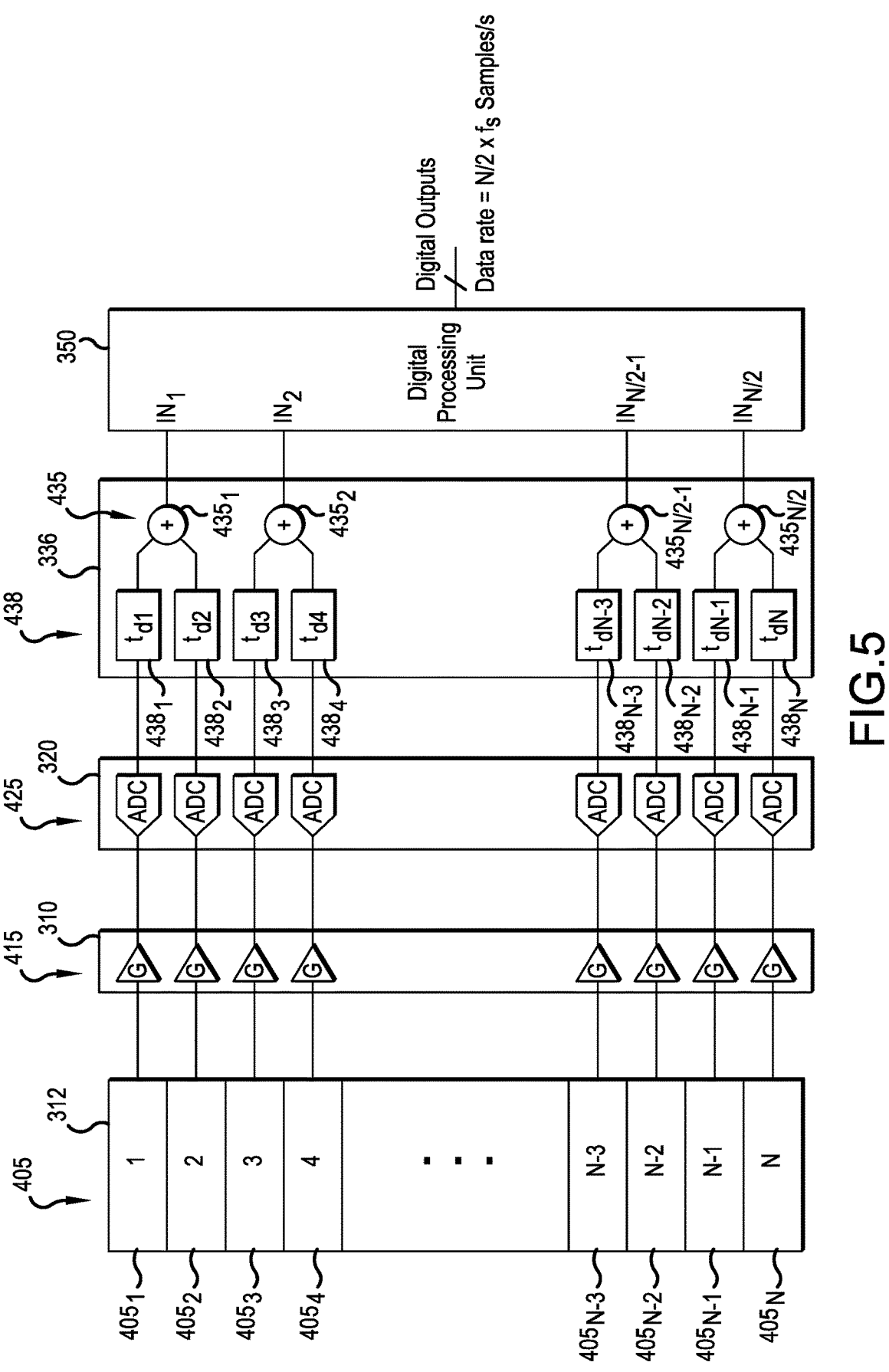
FIG. 5 is a simplified block diagram of a transducer probe in an ultrasound imaging system for reducing digital bandwidth using a beamformer, according to another representative embodiment.

FIG. 5 is a simplified block diagram of a transducer probe in an ultrasound imaging system for reducing digital bandwidth using a beamformer, according to another representative embodiment. The transducer probe is shown configured to receive echo signals reflected in the far field of a medium (e.g., object 105).

Referring to FIG. 5, probe 110 includes the transducer array 312, which includes the multiple transducer elements 405, discussed above. The transducer elements 405 are configured to receive echo signals reflected in the far field, thereby defining a large aperture (e.g., which is larger than the small aperture formed by transducer elements 405 for near field imaging). The transducer elements 405 used to receive the echo signals reflected in the far field may be referred to as the second set of transducer elements. For purpose of illustration, the probe 110 shows the second set of transducer elements consisting of all of the transducer elements 405 to form the large aperture for far field imaging. Of course, the second set of transducer elements may include fewer than all of the transducer elements 405 without departing from the scope of the present teachings. Generally, the far field imaging requirements determine the size of the large aperture for image reconstruction.

The probe 110 further includes the AFE circuit 310 comprising at least the gain controllers 415 and the digitizing circuit 320 comprising the ADCs 425, discussed above. The gain controllers 415 and the ADCs 425 are in channels associated with the transducer elements 405, respectively. In an embodiment, each of the ADCs 425 may have adjustable sampling rates, where the sampling rate for the far field configuration is greater than that of the near field configuration. Generally, fewer transducer elements 405 may be used for near field imaging without affecting quality because there is less signal attenuation of the echoes from the medium over the shorter distances in the near field imaging. So, rather than receiving the echo signals using every transducer element 405, a smaller subset or "patch" of the adjacent transducer elements 405 may be recorded while minimally affecting resolution of the near field images.

The probe 110 further includes the beamformer 336, which includes adders 435 and (optionally) delay circuits 438. In the depicted configuration, representative adders 435 include first adder $435_1$, second adder $435_2$ . . . . $N/2-1^{th}$ adder $435_{N/2-1}$, and $N/2^{th}$ adder $435_{N/2}$. The adders 435 are configured to sum together digitized echo signals in the azimuthal direction received from the ADCs 425 to group the digitized echo signals into respective sub-arrays, which may be referred to as beamforming. For example, the first adder $435_1$ sums digitized echo signals in the channels corresponding to the first transducer element $405_1$ and the first transducer element $405_1$, respectively, the second adder $435_2$ sums digitized echo signals in the channels corresponding to the third transducer element $405_3$ and the fourth transducer element $405_4$, respectively, and so on. The grouping results in fewer digitized echo signals than those provided by all of the transducer elements 405 in the transducer array 312. The transducer elements 405 that provide the digital echo signals to be combined into sub-arrays may be referred to as the second set of transducer elements. In the depicted embodiment, the beamformer 336 is an N:N/2 beamformer, which combines pairs of digital echo signals such that the respective transducer elements 405 are organized into sub-arrays of two. This reduces the number of digitized echo signals output by the beamformer 336 by one half. Operation of the beamformer 336 for combining channels may be performed automatically, e.g., using the processor circuit 210, or manually, e.g., using a user interface or GUI.

The digital processing unit 350 is configured to receive the sub-arrays of digitized echo signals from the beamformer 336, e.g., via near field/far field switch 340 (not shown), and to output a corresponding digital echo data stream that has a smaller digital bandwidth than would otherwise have been present if the digitized echo signals from all of the ADCs 425 would have been processed. When the beamformer 336 is configured as an N:N/2 beamformer, the data rate of the echo data stream is $N/2 \times f_s$ samples/second, where $f_s$ is the frequency of the electrical echo signals output by the transducer elements 405. The echo data stream output by the digital processing unit 350 is communicated to the host system 130 via the communication interface (not shown) and signal conductors 360, where the communication interface has a fixed maximum bandwidth. Operation of the beamformer 336 reduces the number of digital echo signals such that the digital processing unit 350 provides an echo data stream having a total digital bandwidth that is less than the fixed maximum bandwidth of the communication interface.

As mentioned above, the beamformer 336 may further include the delay circuits 438, which may be implemented as a digital RAM or first in first out (FIFO) buffer, for example. In the depicted configuration, representative delay circuits 438 include first delay circuit $438_1$, second delay circuit $438_2$, third delay circuit $438_3$, fourth delay circuit $438_4$, . . . , $N-3^{rd}$ delay circuit $438_{N-3}$, $N-2^{nd}$ delay circuit $438_{N-2}$, $N-1^{st}$ delay circuit $438_{N-1}$, and $N^{th}$ delay circuit $438_N$. The delay circuits 438 are configured to delay the digitized echo signals by respective delay amounts in order to focus the digitized signals at respective pixels being imaged. The delay amounts may be determined by a digital "focus engine" state machine (not shown), as would be apparent to one skilled in the art. The delay amounts may be the same or different amount the delay circuits 438.

Summing the digitized echo signals into sub-arrays reduces the digital bandwidth of the digitized echo signals by a factor of the number of digitized echo signals being added together. In the depicted configuration, for example, each sub-array combines the digitized second echo signals from pairs of the transducer elements 405, where the two transducer elements 405 in each pair are adjacent to one another. Of course, other sizes of sub-arrays and arrangements of transducer elements 405 combined in the sub-arrays may vary without departing from the scope of the present teachings.

The probe 110 also includes the communication interface 355, which is configured to communicate the echo data stream from the digital processing unit 350 to the host system 130 via the signal conductors 360. The adders 335 reduce the digitized second echo signals to a number that provides an echo data stream having a total digital bandwidth that is less than the fixed maximum bandwidth of the communication interface 355.

In various embodiments, the configurations of the probe 110 shown in FIGS. 4 and 5 may be combined to complement one another. For example, the probe 110 may be configured to reduce the digital bandwidth of the echo data stream by utilizing different apertures for receiving echoes in the near field and the far field respectively, where the respective apertures are defined by the number of transducer elements 405. For example, a small aperture comprising fewer than all of the transducer elements 405 (e.g., half (N/2)) may be used for near field imaging and a large aperture comprising all of the transducer elements 405 (N) may be used for far field imaging.

In this example, the transducer elements 405 include the first set of transducer elements made up of half of the total number of transducer elements 405 configured to receive first echo signals responsive to the ultrasound signals being reflected in the near field, and to output corresponding first electrical echo signals. The first set of transducer elements contains fewer than all of the transducer elements 405, thereby defining a small aperture. The transducer elements 405 further include the second set of transducer elements made up of all of the total number of transducer elements 405 configured to receive second echo signals responsive to the ultrasound signals being reflected in the far field, and to output corresponding second electrical echo signals. The second set of transducer elements does not necessarily include all of the transducer elements 405, but does contain more transducer elements 405 than the first set of transducer elements.

Further, in an embodiment, the first electrical echo signals are digitized at a first sampling rate by the ADCs 425 that receive the first electrical echo signals from the selected transducer elements 405 of the small aperture, and the second echo signals are digitized at second sampling rate by the ADCs 425 that receive the second electrical echo signals from the transducer elements 405 of the large aperture, where the first sampling rate is different than the second sampling rate. For example, the first sampling rate may be at least 25 percent greater than the second sampling rate, such as the first sampling rate may be twice the second sampling rate. In this case, the lower sampling rate for the larger number of echo signals from the second set of transducer elements further lowers the digital bandwidth of the echo data stream.

Figure 6:
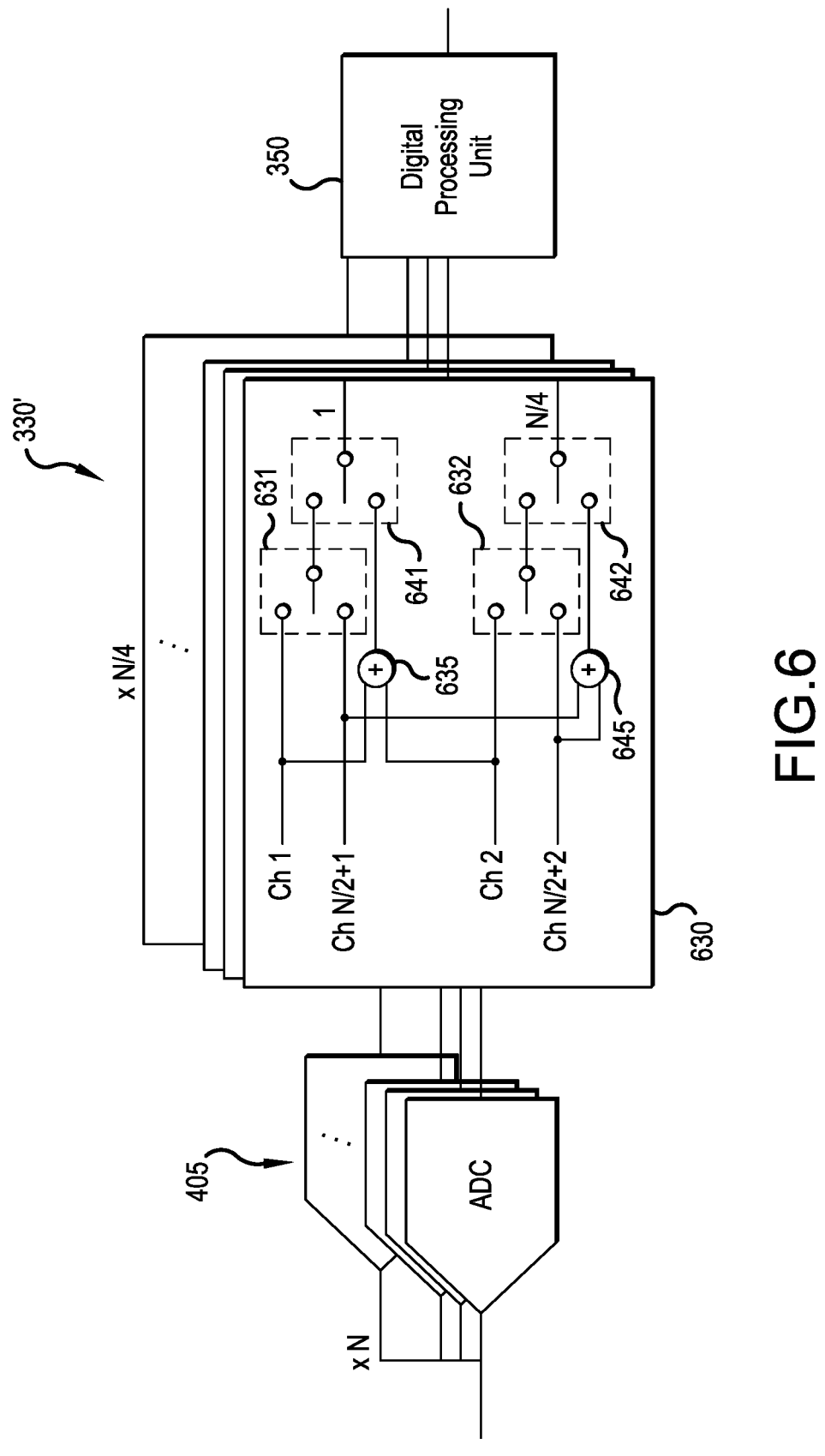
FIG. 6 is a simplified block diagram of a switch circuit for a transducer probe in an ultrasound imaging system for reducing digital bandwidth, according to another representative embodiment.

In an embodiment, the functionality of the multiplexer 334 and the beamformer 336 of the combiner 330 may be combined using a switch circuit. FIG. 6 is a simplified block diagram of the switch circuit for a transducer probe in an ultrasound imaging system for reducing digital bandwidth, according to another representative embodiment.

Referring to FIG. 6, combiner 330' includes a switch circuit 630, which is repeated in parallel multiple times (e.g., four times in the illustrative configuration) to provide sufficient switching capability. The switch circuit 630 is configured to receive digitized echo signals via channels (signal paths) corresponding to the transducer elements 405 providing the echo signals reflected in the near and/or far fields, respectively. Each pair of channels are provided to a multiplexing switch and a beamforming switch, which are activated to select one of the two channels for near field imaging or to combine the two channels for far field imaging. Operation of the switch circuit 630 may be performed by the processor circuit 210, for example.

In particular, the switch circuit 630 includes a first multiplexing switch 631, a first adder 635 and a first beamforming switch 641, and a second multiplexing switch 632, a second adder 645 and a second beamforming switch 642. The first multiplexing switch 631 is configured to select the digitized echo signal from one of a first channel Ch I corresponding to the first transducer element 405₁ or an $$\frac{N}{2} + 1^{st}$$

channel Ch $$\frac{N}{2} + 1$$

corresponding to $$\frac{N}{2} + 1^{st}$$

transducer element (not shown). (The $$\frac{N}{2} + 1^{st}$$

transducer element is the first transducer element of the second half of the N transducer elements.) The first adder 635 is configured to sum the digitized echo signal from the first channel Ch 1 and the second channel Ch 2. The first beamforming switch 641 is configured to select either the multiplexing output of the first multiplexing switch 631 or the sum output of the first adder 635. When the first beamforming switch 641 selects the multiplexing output of the first multiplexing switch 631, the digitized echo signal corresponding to the channel selected by the first multiplexing switch 631 is output from the combiner 330'. When the first beamforming switch 641 selects the output of the first adder 635, the combined (beamformed) digitized echo signals from the first adder 635 is output from the combiner 330'. Similarly, the second multiplexing switch 632 is configured to select the digitized echo signal from one of a second channel Ch 2 corresponding to the second transducer element 405₂ or an $$\frac{N}{2} + 2^{nd}$$

channel Ch $$\frac{N}{2} + 2$$

corresponding to $$\frac{N}{2} + 2^{nd}$$

transducer element (not shown). The second adder 645 is configured to sum the digitized echo signal from the $$\frac{N}{2} + 1^{st}$$

channel Ch $$\frac{N}{2} + 1$$

and the $$\frac{N}{2} + 2^{nd}$$

channel Ch $$\frac{N}{2} + 2^{nd}.$$

The second beamforming switch 642 is configured to select either the multiplexing output of the second multiplexing switch 632 or the sum output of the second adder 645. When the second beamforming switch 642 selects the multiplexing output of the second multiplexing switch 632, the digitized echo signal corresponding to the channel selected by the second multiplexing switch 632 is output from the combiner 330'. When the second beamforming switch 642 selects the output of the second adder 645, the combined (beamformed) digitized echo signals from the second adder 645 is output from the combiner 330''.

Figure 7:
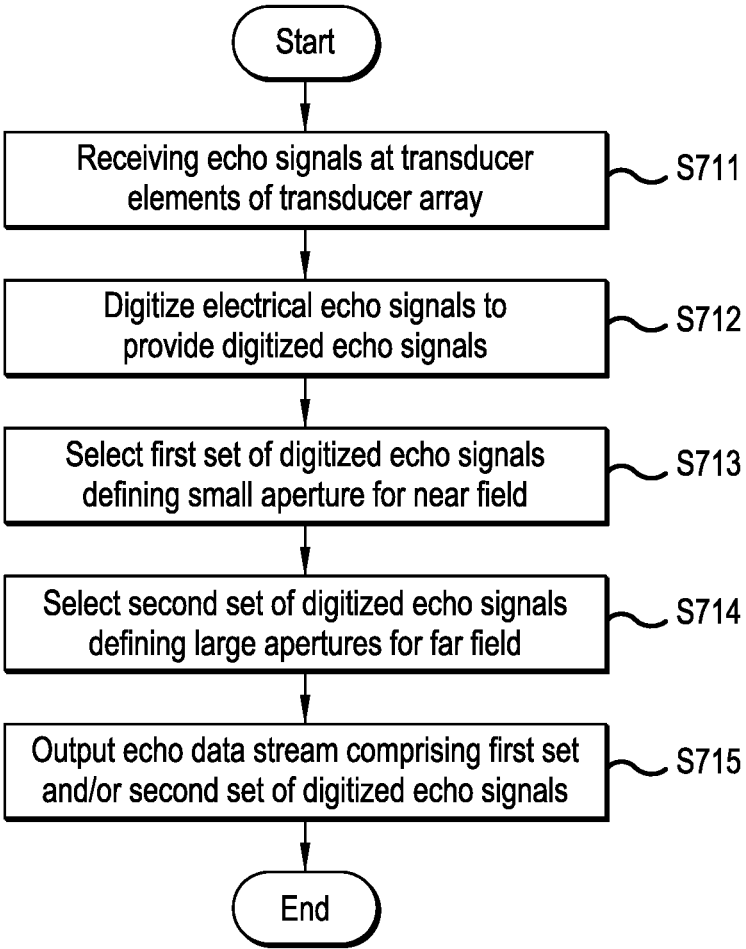
FIG. 7 is a flow diagram of a method for controlling an ultrasound transducer probe including a transducer array having multiple transducer elements, according to a representative embodiment.

FIG. 7 is a flow diagram of a method for controlling an ultrasound transducer probe including a transducer array having multiple transducer elements, according to a representative embodiment. The method may be implemented, for example, using the probe 110, described above.

Referring to FIG. 7, echo signals are received at multiple transducer elements of a transducer array (e.g., transducer array 312) in block S711, and corresponding electrical echo signals are output by the transducer elements. The echo signals are responsive to ultrasound signals emitted by at least some of the transducer elements, where the echo signals are reflected in a near field and/or a far field of a medium (e.g., object 105), such as the anatomy of a patient. The transducer elements may be arranged in a 1. X dimensional transducer array.

In block S712, the electrical echo signals are digitized to provide corresponding digitized echo signals. The electrical echo signals may be digitized by ADCs (e.g., ADCs 425) located in channels corresponding to the transducer elements of the transducer array. In an embodiment, the ADC may digitize the electrical echo signals are different sampling rates, depending on whether the electrical echo signals correspond to echo signals reflected in the near field or the far field. Generally, electrical echo signals corresponding to echo signals reflected in the near field are digitized at a first sampling rate, and electrical echo signals corresponding to echo signals reflected in the far field are digitized at a second sampling rate, where the first sampling rate is higher than the second sampling rate. For example, the first sampling rate may be at least 25 percent greater than the second sampling rate, or the first sampling rate may be at least twice the second sampling rate.

In block S713, a first set of the digitized echo signals is selected for receiving the echo signals reflected in the near field, the first set of the digitized echo signals corresponding to a first set of transducer elements of the multiple transducer elements. The first set of transducer elements contains fewer transducer elements than the total of all of the transducer elements. The first set of transducer elements thereby defines a small aperture.

In block S714, a second set of the digitized echo signals is selected for receiving the echo signals reflected in the far field, the second set of digitized echo signals corresponding to a second set of transducer elements of the multiple transducer elements. The second set of transducer elements contains more transducer elements than the first set of transducer elements. For example, the second set of transducer elements may contain all of the multiple transducer elements. The second set of transducer elements thereby defines a large aperture. The first and second sets of the digitized echo signals may be selected by manual or automatic operation of a switch (e.g., near field/far field switch 340).

The small and large apertures are relative terms in that the small aperture means fewer transducer elements than all of the transducer elements in the transducer array, and the large aperture means more transducer elements than those making up the small aperture. The larger number of transducer elements in the large aperture for far field imaging as compared to the small aperture for near field imaging compensates for the increased attenuation of the echo signals from the medium over the larger distances in the far field imaging. The small aperture typically comprises no more than half of all of the transducer elements in the transducer array, and the large aperture typically comprises all of the transducer elements in the transducer array, although other arrangements of the small and large apertures may be provided without departing from the scope of the present teachings.

In block S715, an echo data stream is output to a host via a communication interface having a fixed maximum bandwidth. The echo data stream includes the first set and/or the second set of the digitized echo signals. The small aperture defined by the first set of transducer elements for the near field imaging provides a digital bandwidth of the echo data stream that is less than the maximum bandwidth of the communication interface. Likewise, the beamforming of the digitized echo signals from the second set of transducer elements for the far field imaging provides a digital bandwidth of the echo data stream that is less than the maximum bandwidth of the communication interface.

Thus, according to the various embodiments, when imaging in the near field, the aperture compared to a total transmit aperture is smaller. Rather than receiving using every channel, a smaller subset (or "patch") of the adjacent channels (signal paths) can be recorded while minimally affecting resolution of the images. In this mode, each of the channels in the patch is configured to receive. The signals are digitized and sent off chip. In comparison to the full aperture needed for the far field, the near field reconstruction may require as few as half the total number of channels, reducing the total necessary data rate. When imaging in the far field, the imaging requirements determine the size of the larger aperture for image reconstruction. In order to reduce the data, sub-arrays (e.g., pairs) of azimuthal channels can be beamformed during receive. The beamformed pairs are then digitized and sent off chip. The beamforming reduces the number of channels digitized by a factor of two, reducing the total necessary data rate. By combining the near field receive profile and far field receive profile, an improved profile can be made that mimics the quality of the larger aperture beam profile with all transducer elements being recorded. This combination effectively reduces the required data rate on an ultrasound imaging system with any number of channels.

Although methods, systems and components for implementing imaging protocols have been described with reference to several exemplary embodiments, it is understood that the words that have been used are words of description and illustration, rather than words of limitation. The preceding description of the disclosed embodiments is provided to enable any person skilled in the art to practice the concepts described in the present disclosure. Thus, to the maximum extent allowed by law, the scope of the present disclosure is to be determined by the broadest permissible interpretation of the following claims and shall not be restricted or limited by the foregoing detailed description.

The Abstract of the Disclosure is provided to comply with 37 C.F.R. § 1.72(b) and is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

The invention claimed is:

1. A transducer probe of an ultrasound imaging system, comprising:
a transducer array comprising a plurality of transducer elements configured to emit ultrasound signals into a medium, to receive echo signals responsive to the ultrasound signals being reflected in a near field and/or a far field of the medium, and to output corresponding electrical echo signals;
a plurality of analog to digital converters (ADCs) configured to digitize the electrical echo signals to provide digitized echo signals;
a combiner configured to process a first set of the digitized echo signals corresponding to a first set of transducer elements of the plurality of transducer elements differently than a second set of the digitized echo signals corresponding to a second set of transducer elements of the plurality of transducer elements, wherein the first set of transducer elements contains fewer transducer elements than the plurality of transducer elements for receiving the echo signals reflected in the near field, thereby defining a small aperture, and wherein the second set of transducer elements contains more transducer elements than the first set of transducer elements for receiving the echo signals reflected in the far field, thereby defining a large aperture, and wherein the combiner further comprises both of a multiplexer configured to multiplex the digitized echo signals to output the first set of the digitized echo signals corresponding to the first set of transducer elements defining the small aperture and a plurality of adders configured to group the transducer elements of the second set of transducer elements into sub-arrays, and to sum together the digitized echo signals from the transducer elements within each sub-array;
a digital processing unit configured to receive the first set of the digitized echo signals and/or the second set of the digitized echo signals, and to output a corresponding digital echo stream; and
a communication interface configured to communicate the echo data stream to an ultrasound imaging system host, wherein the communication interface has a fixed maximum bandwidth,
wherein the small aperture defined by the first set of transducer elements provides a digital bandwidth of the echo data stream that is less than the fixed maximum bandwidth of the communication interface.

2. The transducer probe of claim 1,
wherein the electrical echo signals are digitized at a first sampling rate to provide the first set of the digitized echo signals and the electrical echo signals are digitized at a second sampling rate to provide the second set of the digitized echo signals, wherein the first sampling rate is different than the second sampling rate.

3. The transducer probe of claim 2,
wherein the first sampling rate is at least 25 percent greater than the second sampling rate.

4. The transducer probe of claim 2,
wherein the first sampling rate is twice the second sampling rate.

5. The transducer probe of claim 1, wherein each sub-array contains two of the transducer elements of the second set of transducer elements.

6. The transducer probe of claim 1, wherein the combiner further comprises: a plurality of delay elements arranged prior to plurality of adders, and configured to delay the digitized echo signals by respective delay amounts in order to focus the digitized echo signals at respective pixels being imaged.

7. A method of controlling an ultrasound transducer probe comprising a transducer array having a plurality of transducer elements, the method comprising:
receiving echo signals at the plurality of transducer elements responsive to ultrasound signals emitted by at least some transducer elements of the plurality of transducer elements, wherein the echo signals are reflected in a near field and/or a far field of a medium, and outputting corresponding electrical echo signals;
digitizing the electrical echo signals to provide digitized echo signals;
selecting a first set of the digitized echo signals corresponding to a first set of transducer elements of the plurality of transducer elements, wherein the first set of transducer elements contains fewer transducer elements than the plurality of transducer elements for receiving the echo signals reflected in the near field, thereby defining a small aperture, wherein selecting the first set of the digitized echo signals further comprises multiplexing the digitized echo signals to output the first set of the digitized echo signals corresponding to the first set of transducer elements;

selecting a second set of the digitized echo signals corresponding to a second set of transducer elements of the plurality of transducer elements, wherein the second set of transducer elements contains more transducer elements than the first set of transducer elements for receiving the echo signals reflected in the far field, thereby defining a large aperture, wherein selecting the second set of the digitized echo signals further comprises grouping the transducer elements of the second set of transducer elements into sub-arrays; and summing the digitized echo signals from the transducer elements within each sub-array to reduce a digital bandwidth of the second set of the digitized echo signals; and outputting an echo data stream, comprising the first set of the digitized echo signals and/or the second set of the digitized echo signals to a host system via a communication interface having a fixed maximum bandwidth, wherein the small aperture defined by the first set of transducer elements provides a digital bandwidth of the echo data stream that is less than the fixed maximum bandwidth of the communication interface.

8. The method of claim 7, wherein the electrical echo signals are digitized at a first sampling rate to provide the first set of the digitized echo signals and the electrical echo signals are digitized at a second sampling rate to provide the second set of the digitized echo signals, wherein the first sampling rate is different than the second sampling rate.

9. The method of claim 8, wherein the first sampling rate is at least 25 percent greater than the second sampling rate.

10. The method of claim 8, wherein the first sampling rate is twice the second sampling rate.

11. The method of claim 7, wherein each sub-array contains two of the transducer elements of the second set of transducer elements.

12. The method of claim 7, wherein selecting the first set of the digitized echo signals further comprises:

prior to summing the digitized echo signals from the transducer elements within each sub-array, delaying the digitized echo signals by respective delay amounts in order to focus the digitized echo signals at respective pixels being imaged.

13. A transducer probe of an ultrasound imaging system, comprising:

a transducer array comprising a plurality of transducer elements configured to emit ultrasound signals into a medium, to receive echo signals responsive to the ultrasound signals being reflected in a near field and/or a far field of the medium, and to output corresponding electrical echo signals;

a plurality of analog to digital converters (ADCs) configured to digitize the electrical echo signals to provide digitized echo signals;

a combiner comprising:

a multiplexer configured to multiplex the digitized echo signals to output a first set of the digitized echo signals corresponding to a first set of transducer elements of the plurality of transducer elements defining a small aperture for receiving the echo signals reflected in the near field; and a beamformer comprising a plurality of adders configured to group transducer elements of a second set of transducer elements into sub-arrays providing a second set of digitized echo signals, and to sum together the digitized echo signals from the second set of the transducer elements within each sub-array for receiving the echo signals reflected in the far field, wherein the second set of the transducer elements contains more transducer elements than the first set of the transducer elements;

a digital processing unit configured to receive the first set of the digitized echo signals and the second set of the digitized echo signals, and to output a corresponding digital echo stream; and a communication interface configured to communicate the echo data stream to an ultrasound imaging system host, wherein the communication interface has a fixed maximum bandwidth, wherein the small aperture defined by the first set of the transducer elements provides a digital bandwidth of the echo data stream that is less than the fixed maximum bandwidth of the communication interface.

14. The transducer probe of claim 13, wherein the combiner further comprises:

a sampling rate switch configured to selectively connect the plurality of ADCs to a first signal generator or a second signal generator, wherein the first signal generator is configured to provide a first signal that controls the plurality of ADCs to sample the electrical echo signals at a first sampling rate for near field imaging, and to provide a second signal that controls the plurality of ADCs to sample the electrical echo signals at a second sampling rate for far field imaging, and wherein the first sampling rate is greater than the second sampling rate.

15. The transducer probe of claim 13, wherein the beamformer further comprises:

a plurality of delay elements arranged prior to plurality of adders, and configured to delay the digitized echo signals by respective delay amounts in order to focus the digitized echo signals at respective pixels being imaged.

16. The transducer probe of claim 13, further comprising:

a switch operable to select the multiplexer for near field ultrasound imaging and the beamformer for far field ultrasound imaging.

* * * * *